US008400298B2

(12) United States Patent
Rada

(10) Patent No.: US 8,400,298 B2
(45) Date of Patent: Mar. 19, 2013

(54) DEVICE FOR THE TREATMENT AND EXTRACORPOREAL CIRCULATION OF BLOOD OR BLOOD COMPONENTS

(75) Inventor: Hiram Rada, Lyons (FR)

(73) Assignee: Gambro Lundia AB, Lund (SE)

( * ) Notice: Subject to any disclaimer, the term of this patent is extended or adjusted under 35 U.S.C. 154(b) by 374 days.

(21) Appl. No.: 12/809,032

(22) PCT Filed: Aug. 4, 2008

(86) PCT No.: PCT/IB2008/002033
§ 371 (c)(1),
(2), (4) Date: Jun. 17, 2010

(87) PCT Pub. No.: WO2009/081241
PCT Pub. Date: Jul. 2, 2009

(65) Prior Publication Data
US 2010/0315231 A1    Dec. 16, 2010

(30) Foreign Application Priority Data
Dec. 20, 2007   (FR) ...................................... 07/08917

(51) Int. Cl.
*G08B 21/00*    (2006.01)
(52) U.S. Cl. ......... 340/540; 340/691.1; 340/3.3; 210/85
(58) Field of Classification Search ................... 340/540, 340/573.1, 691.1, 691.6, 693.9, 3.1, 3.3; 210/85, 142, 203, 295, 348; 220/500; 29/428
See application file for complete search history.

(56) References Cited

U.S. PATENT DOCUMENTS

| 5,769,811 | A |   | 6/1998 | Stacey et al. |
| 5,910,252 | A | * | 6/1999 | Truitt et al. .................. 210/645 |
| 6,887,214 | B1 | * | 5/2005 | Levin et al. .................. 604/6.11 |
| 6,923,782 | B2 | * | 8/2005 | O'Mahony et al. .......... 604/4.01 |
| 7,641,626 | B2 | * | 1/2010 | Tonelli et al. ................ 604/4.01 |
| 7,727,391 | B2 | * | 6/2010 | Delnevo et al. ............... 210/252 |
| 2001/0040127 | A1 |  | 11/2001 | Donig et al. |
| 2002/0147423 | A1 |  | 10/2002 | Burbank et al. |
| 2003/0088203 | A1 |  | 5/2003 | Gelfand et al. |
| 2005/0020507 | A1 |  | 1/2005 | Zieske et al. |
| 2005/0131332 | A1 |  | 6/2005 | Kelly et al. |
| 2006/0084906 | A1 |  | 4/2006 | Burbank et al. |

FOREIGN PATENT DOCUMENTS

| DE | 201 13 789 U1 | 5/2002 |
| EP | 0 341 799 A2 | 11/1989 |
| EP | 0 771 569 A2 | 5/1997 |
| GB | 2 310 616 A | 9/1997 |
| WO | 03/026724 A1 | 4/2003 |
| WO | 2004/069299 A2 | 8/2004 |
| WO | 2004/069312 A1 | 8/2004 |
| WO | 2007/061368 A1 | 5/2007 |
| WO | 2007/144427 A2 | 12/2007 |

* cited by examiner

*Primary Examiner* — Toan N Pham
(74) *Attorney, Agent, or Firm* — Pearne & Gordon LLP

(57) ABSTRACT

The invention relates to a medical device for providing a plurality of extracorporeal blood or plasma treatments, apt to receive at least one disposable article that can be connected to extracorporeal circuit, each disposable article being equipped with storage means containing information about the disposable article, the device comprising a first receiving station (2) for disposable articles (100) with a first reading means (3) for the associated article, a second receiving station (3) for disposable articles (100) with a second reading means (3) for the associated article, a memory comprising information concerning at least one treatment protocol designed to be executed by the device, and information concerning a configuration of the disposable articles necessary for each treatment protocol at each receiving station, a control unit (10) for comparing the stored configuration of articles concerning a treatment protocol with the configuration of articles once it is installed.

30 Claims, 12 Drawing Sheets

DEVICE FOR THE TREATMENT AND EXTRACORPOREAL CIRCULATION OF BLOOD OR BLOOD COMPONENTS

TECHNICAL FIELD OF THE INVENTION

The invention relates to a medical device for the treatment and circulation of liquids such as blood or plasma, comprising at least two stations for receiving disposable articles. It can be a machine for extracorporeal blood treatment or for the treatment of renal failure or for receiving and storing liquid from a donor.

PRIOR ART

In the extracorporeal blood treatment blood is taken from a patient, treated in an extracorporeal circuit and returned back to the patient. Extracorporeal blood treatment is used for patients that are not able to effectively remove substances from their blood, for instance in the case of a patient affected by a temporary or permanent kidney failure. In particular, these patients can follow an extracorporeal blood treatment so as to add missing beneficial substances or to remove unwanted substances from their blood, so as to keep an acid-base balance or to remove excess corporeal fluids, for example.

Extracorporeal blood treatment is typically carried out by taking blood from a patient in a continuous flow, introducing blood into a primary compartment of a filter in which blood gets through a semipermeable membrane. The semipermeable membrane selectively lets through unwanted substances contained in blood from the primary compartment to the secondary compartment and can also selectively let through beneficial substances contained in the liquid getting through the secondary compartment through the membrane towards blood getting through the primary compartment, as a function of the type of treatment.

A certain number of extracorporeal blood or plasma treatments can be carried out with the same machine.

In an ultrafiltration (UF) treatment, unwanted substances are removed from blood by convection through the membrane towards the secondary compartment.

In a hemofiltration (HF) treatment, blood flows through the semipermeable membrane as for ultrafiltration, and beneficial substances are added to blood, typically by introducing a fluid into blood, either before (pre-infusion) or after (post-infusion) its passage through the filter and before it is returned back to the patient.

In a hemodialysis (HD) treatment, a secondary fluid containing beneficial substances is introduced into the secondary compartment of the filter. Unwanted substances contained in blood get through the semipermeable membrane and into the secondary fluid, the so-called dialysate, and beneficial substances contained in the secondary fluid can get through the membrane and into blood.

In a hemodiafiltration (HDF) treatment, blood and the secondary fluid exchange their substances as for HD, and moreover, substances are added to blood, typically by introducing a fluid into the treated blood before it is returned back to the patient as for hemofiltration.

In a therapeutic plasma exchange (TPE) treatment, a secondary plasma substitution fluid is introduced downstream from the filter on the venous line, and an effluent lets the used fluid out of the secondary compartment of the filter.

In these treatments, the secondary fluid in the secondary compartment of the filter receives unwanted substances contained in blood by means of the membrane. This liquid is then extracted from the filter: it is commonly known as used liquid and is conveyed towards a drain or a closed container (bag).

Finally, in a hemoperfusion treatment, blood simply gets through a cartridge and a perfusion of anticoagulant is carried out on the arterial line.

It is known about two alternatives for supplying and collecting the various liquids:

the nursing personnel can install the treatment device with an on-line liquid preparation and with an on-line drain. This alternative can be provided for in case of a permanent kidney failure, wherein the patient is subjected to regular, pre-established sessions (e.g. three times a week) of extracorporeal blood treatment with a relatively high blood extraction flow rate, i.e. between 200 and 500 ml/min.

when an on-line liquid preparation is not desirable, the nursing personnel can install and collect liquids in a faster and simpler manner. The user can hang onto the device the supply liquids (dialysis liquids and/or a perfusion liquid), which have already been prepared and stored in sterile disposable bags, and hang an empty disposable bag for collecting used liquid. This case can be provided for in case of a temporary kidney failure, the patient will have to be treated in an emergency condition and be subjected to a continuous and long extracorporeal blood treatment with a relatively low blood extraction flow rate, or in case of daily dialysis wherein the patient himself prepares the machine.

In this second case where ready-to-use bags are used, the international application WO2004/069312 issued to the Applicant describes a treatment machine comprising several devices for supporting such containers (bags). This application is herein incorporated by reference. The machine according to this prior art is shown in FIG. 1: this machine (1000) comprises a support device under the housing (27) of the machine, apt to house bags (1001) in the lower portion of the machine. Several similar bag support devices are installed at the same lower level of the machine.

The user rapidly or simply hangs onto the device a dialysis liquid and/or a (several) perfusion liquid(s), which have already been prepared and stored in a sterile disposable bag, and hangs an empty disposable bag for collecting used liquid.

During the treatment session of the machine according to the invention, which proposes a selection of several treatments, the user of the machine chooses the treatment protocol which is most suitable among the protocols referred to above: HD, HDF, UF, HF, TPE . . . . It should be pointed out that, depending on the protocol that has been chosen, different disposable articles are required in different receiving stations.

Depending on the selected treatment, before starting the treatment the user will have to install and connect to the hydraulic circuit one or more disposable, ready-to-use articles on one or more corresponding supports. Indeed, the article to be fastened or not corresponds to each specific support.

Some drawbacks might occur in case of an incorrect installation of the articles, such as solution bags, and the invention aims at avoiding such drawbacks.

As a matter of fact, it should be pointed out that the various articles used have a similar or identical capacity and appearance. Moreover, some articles have use specifications: for instance, a bag can include two compartments containing two solutions that have to be contacted immediately before use. In an intensive care unit, for instance, the user must prepare as fast and simply as possible the extracorporeal blood or plasma treatment machine and must identify, select and fasten the necessary articles for the treatment, before starting the machine.

An article might be missing, an article might be in excess, an article might be installed on the incorrect support, or two articles might be installed on reversed supports. The user might forget to mix the content of the two compartments of an article.

A problem which the invention aims at solving is therefore to increase the safety level for the installation of the articles in suitable receiving stations of the medical device.

Another problem solved by the invention is to check the correct installation of the necessary articles.

Another problem that has been solved is a problem of traceability of used articles.

A further problem is to record data concerning the use that will have been made of the article.

It should be noted that it is further known from application US2003/0088203 about a blood treatment device apt to receive a disposable set made up of a dialyzer and lines pre-connected to the dialyzer and forming the extracorporeal hydraulic blood circuit. This disposable set is equipped with a storage key (e.g. chip) containing information about the set (calibration for sensors, model and manufacturing date, owner's secret code). This key is on the set or associated thereto and is enabled by the machine at the beginning of the patient's treatment, so as to prevent the set from being re-used or from being used at a delayed time, patient data can be stored in the key during the treatment.

DESCRIPTION OF THE INVENTION

The invention relates to a medical device (1) for providing a plurality of extracorporeal blood or plasma treatments in a filtration unit having a primary compartment and a secondary compartment, which are separated by a semipermeable membrane, the primary compartment being able to be connected to a primary extracorporeal blood circuit, the secondary compartment being able to be connected to a secondary circuit, the primary circuit and the secondary circuit defining the extracorporeal circuit, the device being apt to receive at least one disposable article that can be connected to the extracorporeal circuit, each disposable article being equipped with storage means containing information about the disposable article, the device comprising:
- a first receiving station (2) for disposable articles (100), which is able to collect a first disposable article,
- a first reading means (3) associated to the first station (2) for identifying a disposable article (100) that may have been received at the first station (2),
- at least a second station (2') for receiving disposable articles (100), which is able to collect a second similar disposable article (100'),
- at least a second reading means (3') associated to the second station (2') for identifying a disposable article (100') that may have been received at the second station,
- a storage means (11) for storing:
    - information concerning at least one treatment protocol designed to be executed by the device,
    - information concerning a configuration of the disposable articles necessary for each treatment protocol at each receiving station,
- a control unit (10) connected to the storage means (11), comprising:
    - means for receiving information concerning the treatment protocols to be executed,
    - means for receiving information read by at least one of the reading means, and
    - means for checking, as a function of this information, whether the configuration of the disposable article or articles received complies with the stored configuration for the treatment to be executed.

The invention also relates to this medical device wherein at least one disposable medical article (100) is installed in at least one receiving station (2).

The invention also relates to a kit of containers (100, 100', 100", 100''') for liquids for medical use, this kit being designed to be used and fastened onto a medical device (1) for executing a plurality of extracorporeal blood or plasma treatments and comprising several receiving stations (2, 2' . . . ) for containers, each having a fastening means (5, 5' . . . ) for containers, the fastening means for containers being identical, each station having a reading means (3, 3' . . . ) associated thereto for the identification of the container to be received, and wherein:

Each container is equipped with a storage means (101, 101' . . . ) for storing:
    a. information concerning at least one treatment protocol designed to be executed by the device,
    b. information concerning a configuration of the disposable articles necessary for each treatment protocol at each receiving station.

The invention also relates to a container comprising a first compartment containing a first fluid for medical use, at least a second compartment containing a second fluid for medical use, a fluid communication means between the first and the second compartment, a closing means for the fluid communication means between the compartments, the closing means being removable so as to enable the communication between the two compartments, characterized in that at least one of the two compartments contains a storage means for storing:
    a. information concerning at least one treatment protocol designed to be executed by the device,
    b. information concerning a configuration of the disposable articles necessary for each treatment protocol at each receiving station,
and in that the storage means is able, once the closing means is removed from said fluid communication means, to switch from the first to the second compartment.

The invention further relates to a control method for the device (1) according to the invention, wherein at least one disposable medical article (100) is installed in at least one of the receiving stations (2), the device comprising an interface (12), the method comprising at least the following steps:
- receiving by way of the interface (12) the selection of an extracorporeal treatment among the plurality of possible treatments stored,
- reading the storage means (101) for each disposable article installed in the receiving station or stations (5) by way of each reading means (3) associated thereto,
- comparing the installation configuration of the articles once they are installed in the receiving stations with the required stored configuration of disposable articles necessary for the selected treatment,
- sending by way of the display means (13) an alarm or warning signal when the configuration of the installed articles does not correspond to the required stored configuration.

Finally, the invention relates to a method for installing disposable articles in a device according to the invention, comprising the following steps:
- selecting an extracorporeal treatment among the plurality of possible stored treatments,
- installing the medical article or articles (100 . . . ) in the receiving station or stations (2 . . . ), reading the storage means (101 . . . ) for each disposable article installed in the receiving station or stations (2 . . . ) by way of each reading means (3 . . . ) associated thereto, comparing the configuration of the articles installed in the receiving stations with the required stored configuration of disposable articles for the selected treatment, if the configuration of the installed articles is not identical to the required stored configuration, sending an alarm or warning signal, as a function of the sending of an alarm or warning message, add, remove or change at least one disposable medical article.

SHORT DESCRIPTION OF THE DRAWINGS

Other advantages and characteristics of the invention will be more evident from the following description. Reference will be made to the attached drawings representing non-limiting examples of the invention, in which.

FIGS. 8 to 13 show the hydraulic operating diagram and the corresponding configuration of liquid containers for the following protocols in this order: hemodiafiltration, hemodialysis, hemofiltration with perfusion upstream and/or downstream from the filter, ultrafiltration, therapeutic plasma exchange, hemoperfusion. The hydraulic circuits shown herein contain additional elements (bubble trap, air detector, pressure measurement, blood leak detector, venous line clamp . . . ), which should not be considered as limiting.

DETAILED DESCRIPTION OF EMBODIMENTS OF THE INVENTION

Figure 13:
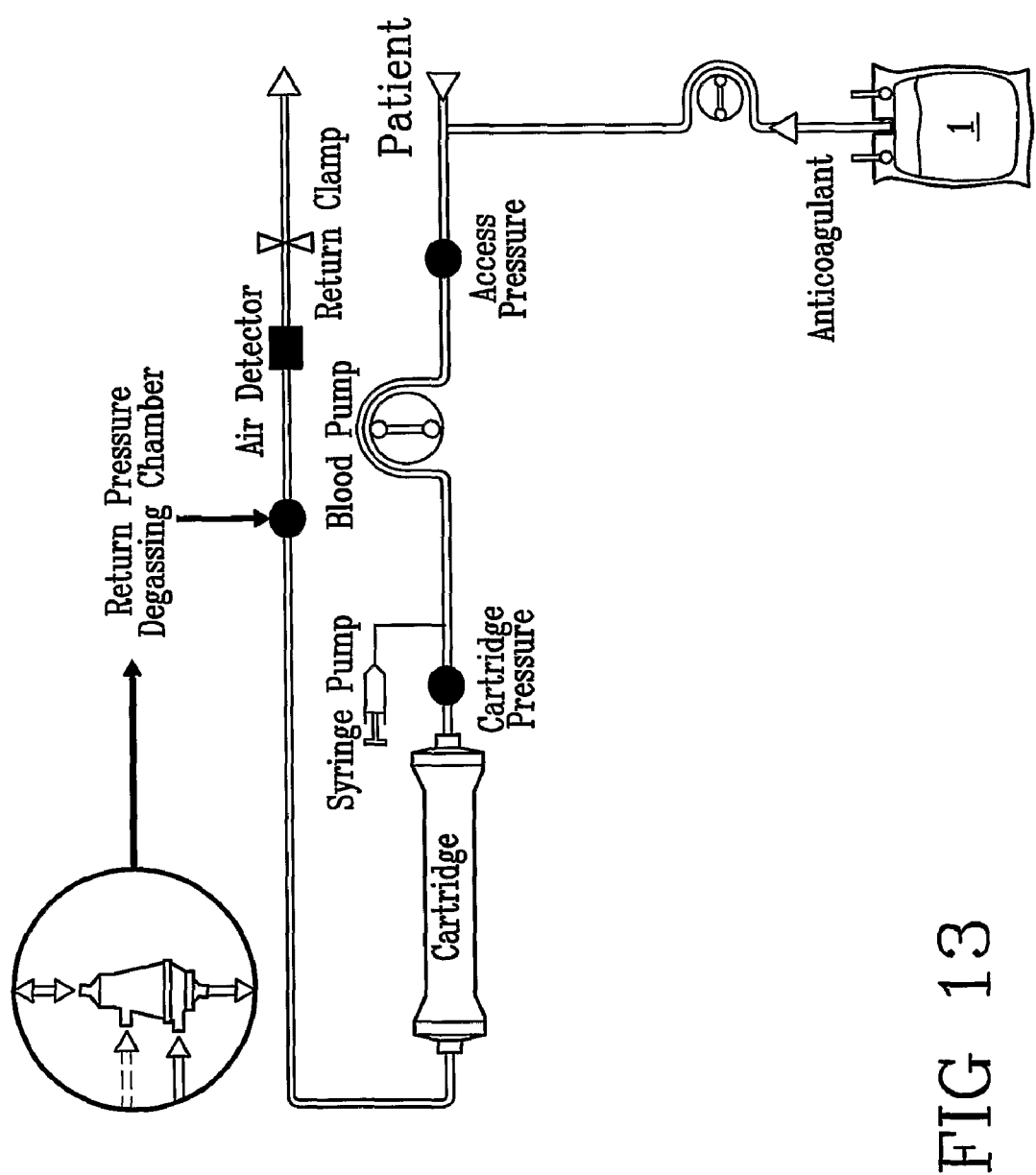

The invention relates to a medical device 1 for providing a plurality of extracorporeal blood or plasma treatments. Blood treatment can be a treatment in a filtration unit having a primary compartment and a secondary compartment, which are separated by a semipermeable membrane, the primary compartment being able to be connected to a primary extracorporeal blood circuit, the secondary chamber being able to be connected to a secondary circuit, the primary circuit and the secondary circuit defining the extracorporeal circuit. For hemoperfusion, as shown in FIG. 13, the filter is replaced by a one-compartment adsorption cartridge. The device is apt to receive at least one disposable article that can be connected to the extracorporeal circuit.

Each disposable article is equipped with storage means containing information about the disposable article.

The device comprises:

a first receiving station (2) for disposable articles (100), which is able to collect a first disposable article, a first reading means (3) associated to the first station (2) for identifying a disposable article (100) that may have been received at the first station (2), at least a second station (2') for receiving disposable articles (100), which is able to collect a second similar disposable article (100'), at least a second reading means (3') associated to the second station (2') for identifying a disposable article (100') that may have been received at the second station, a storage means (11) for storing:
information concerning at least one treatment protocol designed to be executed by the device,
information concerning a configuration of the disposable articles necessary for each treatment protocol at each receiving station, a control unit (10) connected to the storage means (11), comprising:
means for receiving information concerning the treatment protocols to be executed,
means for receiving information read by at least one of the reading means, and
means for checking, as a function of this information, whether the configuration of the disposable article or articles received complies with the stored configuration for the treatment to be executed.

The means of the control unit (or CPU) are instructions loaded onto the programmable unit of the control unit.

Figure 1:
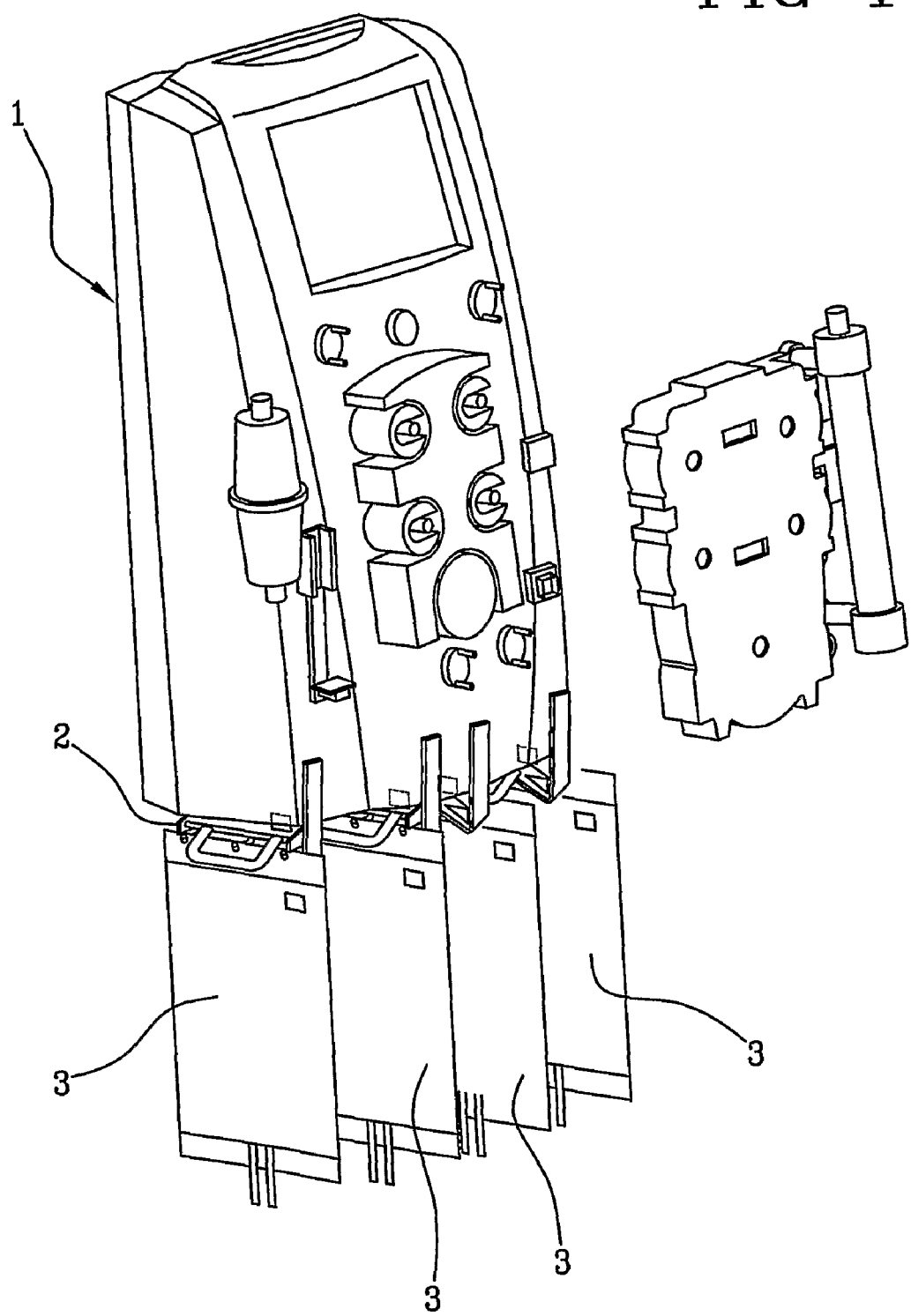
FIG. 1 shows a medical device according to the prior art WO2004/069312.
Figure 2:
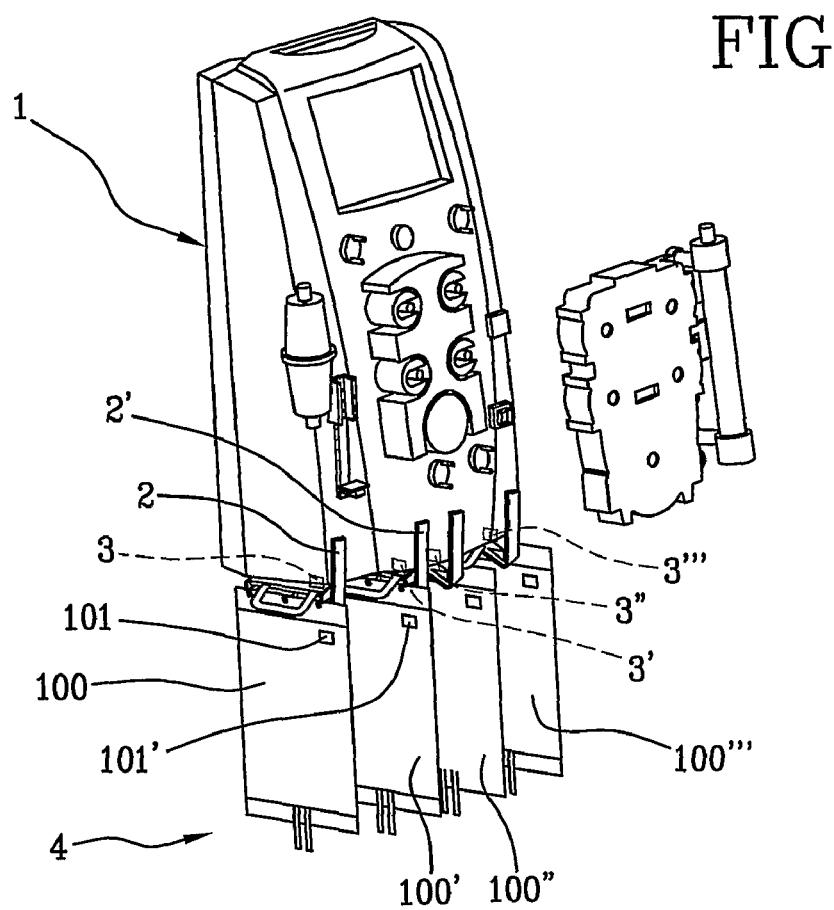
FIGS. 2 and 3 show the device according to the invention and a view of the lower portion of the device according to the invention.
Figure 3:
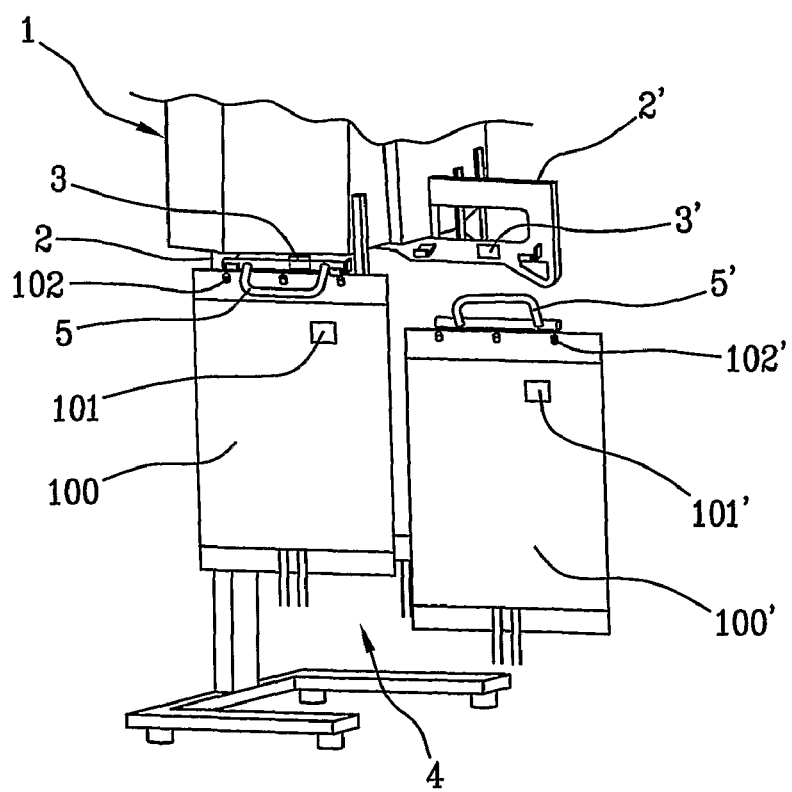

The device is shown by way of example in FIGS. 2 and 3.

Figure 4:
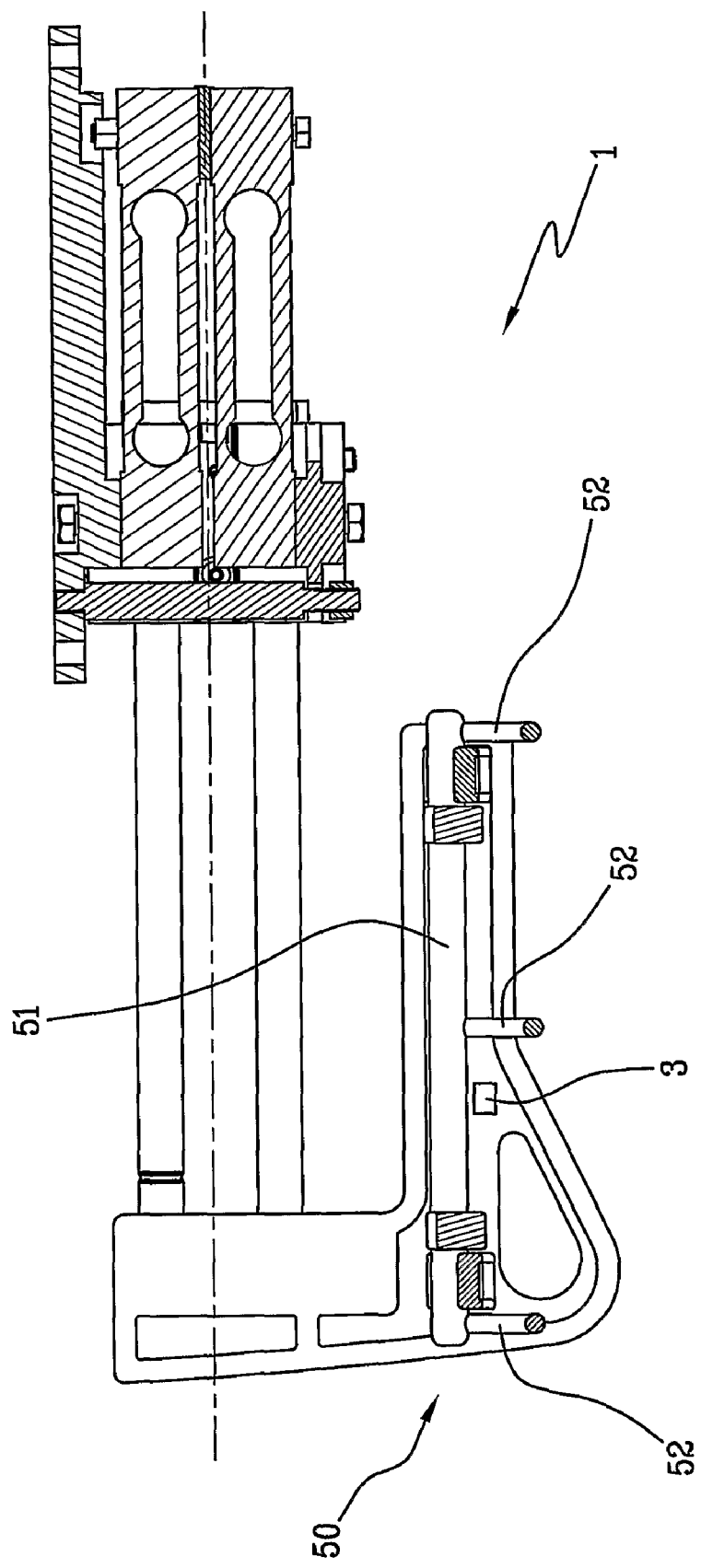
FIG. 4 shows a portion of the receiving station comprising the fastening means for the expected medical article.

FIG. 4 shows an example of receiving station according to the invention. This receiving station comprises a portion that can shift between two positions. The first position is a non-operating loading position, wherein the portion is outside the space limited by the machine and enables the disposable bag to be easily loaded or unloaded. The second position is an operating treatment position, wherein the portion is in the lower space of the machine and supports the bag being used. The support 50 comprises a basis body, made up of a bar 51, on which at least one hook 52 is fastened (three hooks in FIG. 4) for receiving the treatment liquid bag containing as many holes as the hooks. The reading means 3 is placed at the same level on the mobile portion between the two positions. However, this means can alternatively be placed on a fixed portion of the machine close to the mobile portion when in loading position.

For more details reference can be made to the description of this FIG. 4 in WO2004/069312.

For the device according to the invention, the configuration of the disposable articles necessary for each protocol comprises at least one of the following elements for each treatment protocol: the number of necessary articles, the type of each necessary article, the function of each necessary article (e.g. a drug, a medical fluid . . . ), the position of each necessary article in each receiving station.

The first receiving station (2) can comprise first fastening means (5) for articles (1), at least the second receiving station (2') for articles can comprise second fastening means (5') for the article that are identical to the first fastening means (5) for articles. As a matter of fact, if the articles can differ from a visual point of view, if the fastening means are identical, the user can make mistakes when executing the installation. More particularly, the receiving station can be completely identical to one another.

Similarly, the disposable article (100) that can be received in the first receiving station (2) comprises first fastening means (102) to a receiving station (2), at least the second disposable article (100') that can be received in the second receiving station (2') comprises second fastening means (102') to a receiving station that are identical to the first fastening means (102) of the station. More particularly, the articles can be identical in their external structure, such as for instance liquid containers which are identical and differ only in the liquid they contain.

The control unit (10) according to the invention comprises means (instructions loaded onto the programmable unit of the control unit) for sending an alarm signal as a function of said information, if the configuration of the disposable article or articles received does not comply with the configuration of the selected treatment.

The device according to the invention comprises display means (13) such as a screen, illuminated buttons or any other type of display device. The control unit (10) then comprises means for controlling the display means (13) as a function of said information, i.e. information concerning at least one treatment protocol designed to be executed by the device, and information concerning a configuration of the disposable articles necessary for each treatment protocol at each receiving station. The display means therefore enable to display an alarm message or a warning message comprising at least one of the following information:
  a necessary article is missing in the device,
  an unnecessary article is present in the device,
  a necessary article is present but is installed in an incorrect receiving station,
  a necessary article is present in the device,
  a present article requires a particular use, e.g. a preparation previous to the use of the article.

The device according to the invention is provided with storage means (11) that are able to store all the information received by the reading means associated to the receiving stations. The information about the disposable articles used are thus stored in the storage means from one use to another. These stored data can obviously be together with other data: the patient's identity, the patient's clinical data, the evolution of machine parameters (e.g. flow rate of pumps used) and of patient parameters (e.g. arterial pressure, weight loss . . . ) during the session: this enables to store a history of all parameters involved in the selected treatment.

Figure 5:
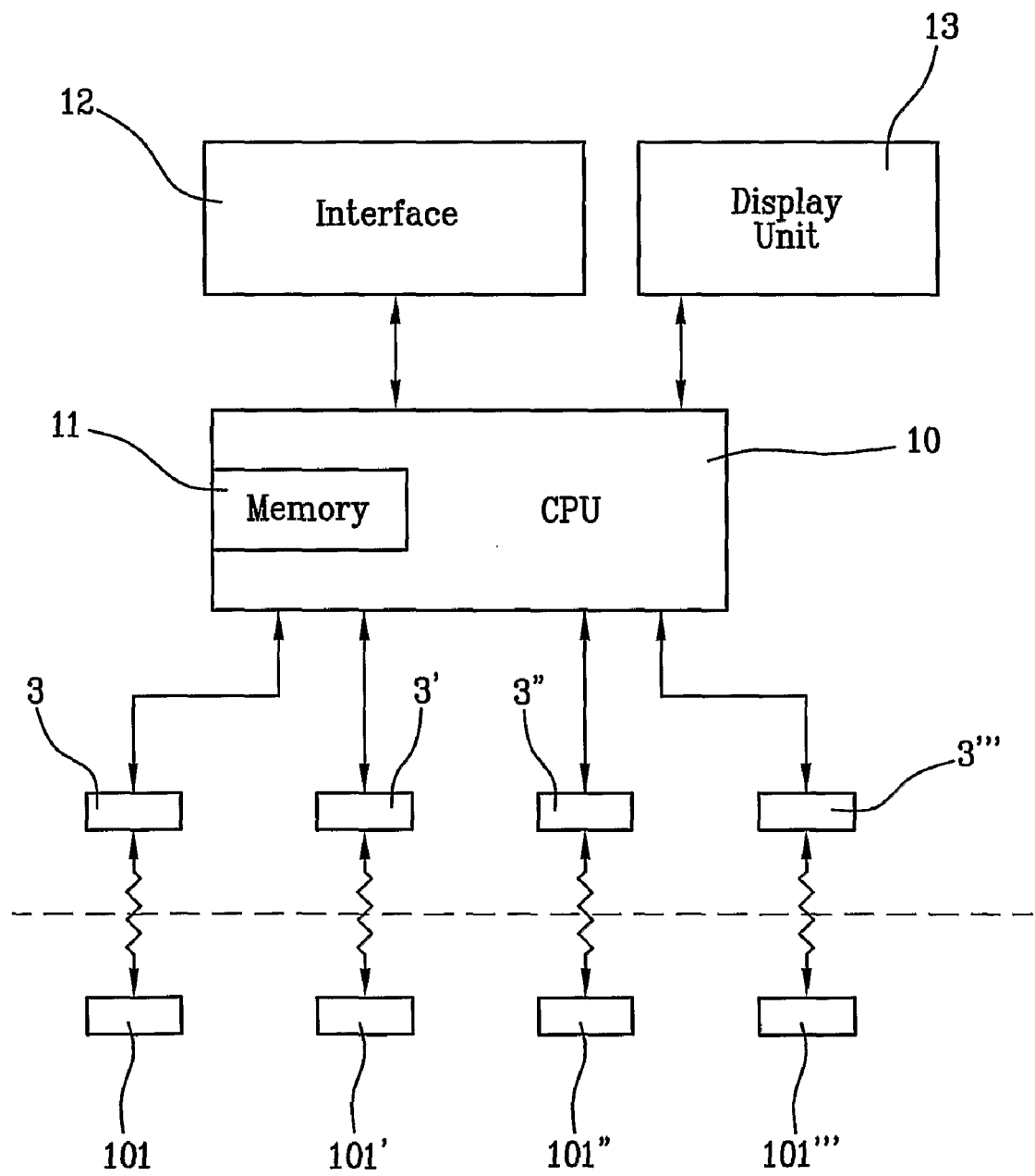
FIG. 5 shows the basic electronic configuration according to the invention.

FIG. 5 schematically represents the electronic configuration of the invention, comprising the control unit 10, containing or connected to the memory 11, being able to communicate uni- or bidirectionally with the interface (touchscreen, keyboard), the display unit (screen, illuminated button), and each of the reading means (3) associated to the receiving stations. The reading means (3) can communicate with the respective memories (101 . . . ) of the disposable articles. The user can thus enter by means of the interface the selected treatment protocol and can display the alarm or warning or checking messages. He can validate or not warnings, cancel or not alarms, validate or not checking messages.

The device according to the invention can include:
  at least one reading means (3, 3', 3", 3"') integrated into the associated receiving station (2, 2', 2", 2"'),
  at least one reading means (3, 3', 3", 3"') close to the associated receiving station (2, 2', 2", 2"').

In the case of an integrated means, as shown in the figures, the reader is part of the receiving station.

In the case of a close means, not shown in the figures, the reader can be in the upper portion of the machine close to the receiving station, or in the lower portion of the machine, e.g. in the base of the machine.

In all cases, when the reader is contactless, it is advisable to place each reader close to the article identification means (once the article is installed), but obviously so that only the reader can get in contact with the corresponding article identification means, and not with the identification means of the adjacent article: reader position, field and intensity are parameters to be kept into account.

In the case of an integrated means, the receiving station or stations (2, 2', 2", 2"') can be more specifically a weighing means for weighing the disposable device to be received, as shown in the figures. As a matter of fact, this weighing means is present and, when the articles are liquid containers, enables to follow the weight evolution of the liquids contained in the liquid containers. These weight indicators would have an additional function, preventing at the same time to increase the overall size of the various elements of the machine.

The device according to the invention can comprise at least one reading means (3, 3', 3", 3"') which is a contactless reading means. Such a contactless reading means is included among at least one of the following readers:
  a radiofrequency reading means (reader known as "RFID"),
  an optical reader: for instance, a bar code reader or a code color reader or a reader of any shape and/or model that can be optically detected:
  a magnetic reader, for instance a magnetic tape reader,
  or any equivalent reader apt to detect said information when the element and the reading portion are one close to the other (touch each other or are adjacent one to the other).

The device according to the invention can be designed to receive disposable articles (100, 100', 100", 100"') belonging to one of the following categories:
  container comprising a medical liquid such as a bag or a syringe,
  empty container designed to receive used liquid,
  dialyzer,
  set containing at least one filter with various accesses (inlets and outlets) and lines connected to the accesses of the filter so as to form at least partially the extracorporeal circuit: this type of so-called set is an article pre-connected to lines, which is installed directly into the machine and enables to spare the time required for connecting lines to the filter,
  blood or plasma filter, absorption cartridge,
  ultrafilter, plasma filter.

The device according to the invention can include:
  a plurality of first receiving stations (2, 2') comprising first respective identical fastening means (5, 5') for fastening a first category of disposable articles (100, 100'),
  at least a plurality of second receiving stations (2", 2"') comprising second respective identical fastening means (5", 5"') for fastening a second category of disposable articles (100", 100"'), the second fastening means (5", 5"') being different from the first fastening means (5, 5'),
  and wherein the first category and the second category of disposable articles are each included among one of the following categories:
    container comprising a medical liquid such as a bag or a syringe,
    empty container designed to receive used liquid,
    dialyzer,
    set comprising at least one filter containing various accesses and lines connected to the accesses of the filter so as to form at least partially the extracorporeal circuit,
    blood or plasma filter, absorption cartridge,
    ultrafilter,
    plasma filter.

For instance, receiving stations for containers of medical liquid (e.g. other stations) can be envisaged as first receiving stations, and receiving stations for dialyzers (e.g. two stations) can be envisaged as second receiving stations.

More precisely, the category of disposable articles can be a category "container" containing a medical liquid, more specifically it can be a bag for a medical liquid. For instance: the disposable articles comprise at least one of the following bags: a bag filled with dialysis liquid, a bag filled with perfusion liquid, a bag filled with anticoagulant, an empty bag for receiving during treatment used medical liquid. This set allows to carry out the treatments HD, HF, HDF, UF.

Figure 6:
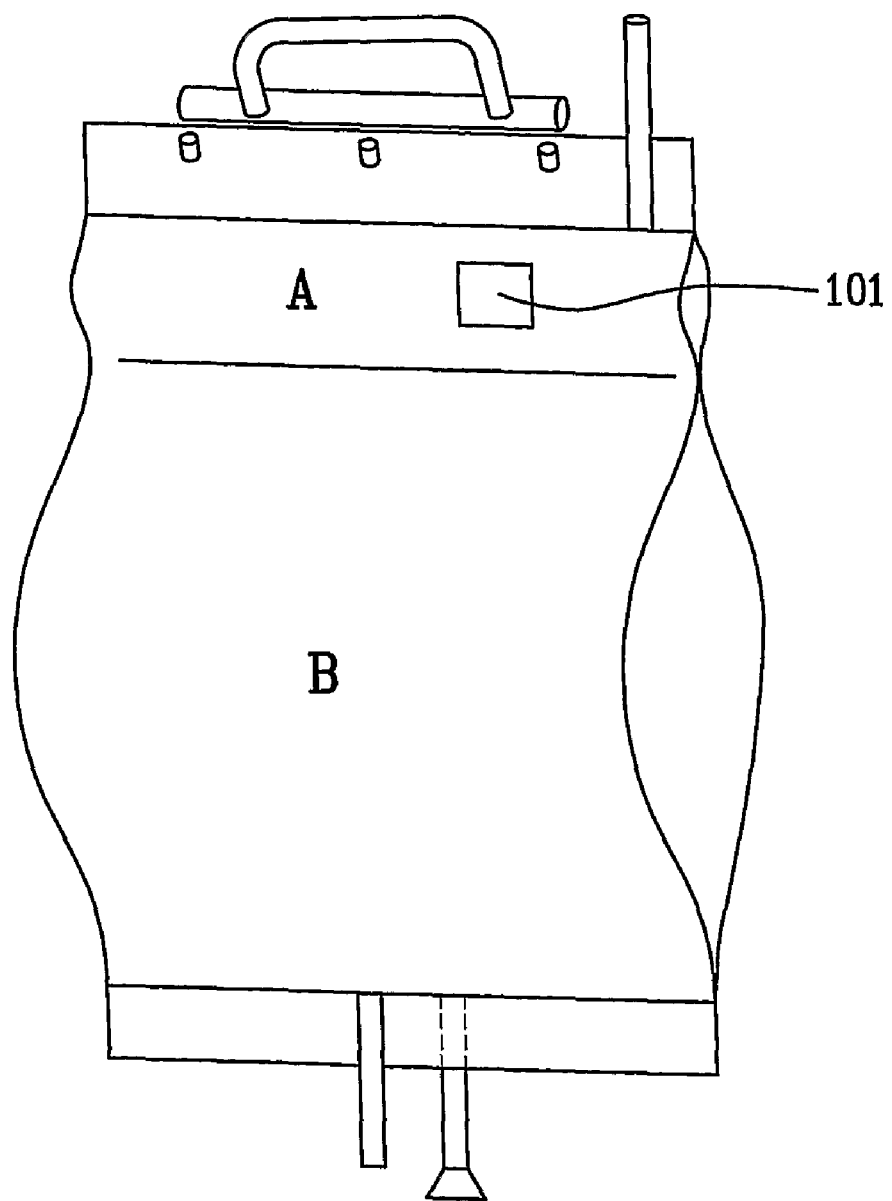
FIG. 6 shows a diagram of a disposable article being a two-compartment bag.

The device according to the invention can receive at least one of the disposable articles (100) which is a container provided with at least two compartments, the compartments containing each a liquid for medical use, as shown in FIG. 6. The bag comprises several accesses and has two compartments A and B with a fluid communication means closed between the two compartments during storage and open (e.g. plastic barrier to be broken) before using the device. These containers are for instance bags and are characterized by a mode of use according to which the liquids of each compartment have to be mixed immediately before use in the device (e.g. an article marketed by the Applicant under the name "Prismocal"). As an alternative, for some treatment protocols using certain medical fluids, the pre-mixing of the two compartments is not foreseen.

More specifically, the device according to the invention can be a blood or plasma treatment device having a filtration unit with a semipermeable membrane dividing the unit into a first compartment and a second compartment. The primary circuit is defined by the arterial line for taking blood from the patient, the primary compartment of the filtration unit and the venous line for returning blood back to the patient. The secondary circuit is made up of at least the secondary compartment of the filtration unit, and if necessary of a line conveying dialysis liquid into the secondary compartment, if necessary of a line for letting used dialysis liquid get out towards a drain, and if necessary of one or more lines for introducing substitution liquid into the primary circuit.

This device is equipped with:
- its first receiving station (2) designed to receive a container of perfusion liquid to be connected to the arterial line of the primary circuit,
- its second receiving station (2') designed to receive a container of fresh dialysis liquid to be connected to the inlet of the secondary compartment of the filtration unit, and also comprises:
- a third receiving station (2") for disposable articles, similar to the first and second receiving stations and designed to receive a third disposable article, the third article being a container of perfusion liquid to be connected to the primary circuit upstream or downstream from the first compartment of the filtration unit,
- at least one third reading means (3") associated to the third station (2") for identifying the disposable article that may have been received at the third station,
- a fourth receiving station (2''') for disposable articles, similar to the first three receiving stations and designed to collect an empty fluid container to be connected to the outlet of the secondary compartment of the filtration unit.

The perfusion liquid includes several types of liquids, among which: substitution liquids, to be perfused with pre-dilution (a dilution carried out on a fluid before it gets through the filter) or to be perfused with post-dilution (a dilution carried out after getting through the filter), or also anticoagulant liquids such as heparin, citrate . . . .

This device is therefore provided with storage means (11) comprising at least one of the following protocols:
a) a first protocol of treatment by hemodiafiltration (e.g. CVVHDF, shown in FIG. 8) requiring the presence of four medical articles on the four corresponding receiving stations,
b) a second protocol of treatment by hemodialysis (e.g. CVVHD, shown in FIG. 9) requiring the presence of the first, second and fourth medical article on the corresponding first, second and third receiving station,
c) a third protocol of treatment by hemofiltration (e.g. CVVH, shown in FIG. 10) requiring the presence of the four medical articles on the four corresponding receiving stations,
d) a fourth protocol of treatment by ultrafiltration (e.g. SCUF, shown in FIG. 11) requiring the presence of the first and fourth medical article on the corresponding first and fourth receiving station,
e) a fifth treatment protocol by plasma exchange (TPE, shown in FIG. 12) requiring the presence of the first, second and fourth medical article on the corresponding first, second and fourth receiving station,
f) a sixth protocol of treatment by hemoperfusion (HF, shown in FIG. 13) requiring the presence of the first medical article on the corresponding fourth receiving station.

The articles are therefore containers for medical liquids.

The following contains tables as non-limiting examples for each treatment as proposed above, with several possible sets of medical bags to be installed onto four weight indicators: "weight indicator PBP (pre-blood pump, pump on the arterial line of the extracorporeal circuit)" corresponding to the first receiving station, "weight indicator dialysate" corresponding to the second receiving station, "weight indicator substitution" corresponding to the third receiving station, "weight indicator effluent" corresponding to the fourth receiving station.

There is a list of the examples of possible combination of solution bags, whether the absence or presence is mandatory or recommended, which function the solution contained in the bag has, whether a prohibition of nature of solution is prescribed, and whether a condition of use has to be recommended or checked and validated by the user.

Example 1

CVVHDF with Perfusion PRE or POST Filtration Unit: Hydraulic Diagram FIG. 8

| Check | Weight indicator PBP: detector | Weight indicator Dialysate: detector | Weight indicator Substitution: detector |
|---|---|---|---|
| Presence of solutions (first possibility) | Prismocitrate | Prism0cal 2 pockets | Prism0cal 2 pockets |

-continued

| Check | Weight indicator PBP: detector | Weight indicator Dialysate: detector | Weight indicator Substitution: detector |
|---|---|---|---|
| Presence of solutions (second possibility) | ACD-A | PrismOcal 2 pockets | PrismOcal 2 pockets |
| Presence of solutions (third possibility)) | Hemosol 2 pockets | Hemosol 2 pockets | Hemosol 2 pockets |
| Presence or absence? | No recommendation | Mandatory presence | Mandatory presence |
| Function of solution? | Drug Possible medical device under physician's responsibility | No recommendation | Drug Possible medical device under physician's responsibility |
| Prohibition of nature | No recommendation (or prism0cal not recommended) | Prohibition of Prismocitrate | Prohibition of Prismocitrate |
| Conditions of use | | If two-compartment mixing check to be confirmed. Confirm whether Hemosol is used with Prismocitrate or ACD-A. | If two-compartment mixing check to be confirmed. Confirm whether Hemosol is used with Prismocitrate or ACD-A. |

"Weight indicator effluent": it has been chosen not to install or use reading means at the corresponding receiving station.

The liquids Prismocitrate, ACD-A, Hemosol, PrismOcal are marketed by the Applicant.

Example 2

CVVHD: Hydraulic Diagram FIG. 9

| Check | Weight indicator PBP: detector | Weight indicator Dialysate: detector | Weight indicator Substitution: detector |
|---|---|---|---|
| Presence of solution | Prismocitrate | PrismOcal 2 pockets | |
| Presence of solution | ACD-A | PrismOcal 2 pockets | |
| Presence of solution | Hemosol | Hemosol | |
| Presence or absence | No recommendation | Mandatory presence | Mandatory absence |
| Function of solution | Drug Possible medical device under physician's responsibility | No recommendation | |
| Interdiction de nature | No recommendation | Prohibition of Prismocitrate | |
| Condition of use | (or prism0cal not recommended) | If two-compartment mixing check to be confirmed. Confirm whether Hemosol is used with Prismocitrate or ACD-A. | |

"Weight indicator effluent": it has been chosen not to install or use reading means at the corresponding receiving station.

Example 3

CVVH: PRE and/or POST: Hydraulic Diagram FIG. 10

| Check | Weight indicator PBP: detector | Weight indicator Dialysate: (pre) detector | Weight indicator Substitution: (pre or post) detector |
|---|---|---|---|
| Presence of solution | Prismocitrate | Prism0cal 2 pockets | Prism0cal 2 pockets |
| Presence of solution | ACD-A | Prism0cal 2 pockets | Prism0cal 2 pockets |
| Presence of solution | Hemosol | Hemosol | Hemosol |
| Presence or absence | No recommendation | Mandatory presence | Mandatory presence |
| Function of solution | Drug Possible medical device under physician's responsibility | Drug Possible medical device under physician's responsibility | Drug Possible medical device under physician's responsibility |
| Prohibition of nature | No recommendation | Prohibition of Prismocitrate | Prohibition of Prismocitrate |
| Condition of use, recommendation | (or prismocal not recommended) | If two-compartment mixing check to be confirmed. Confirm whether Hemosol is used with Prismocitrate or ACD-A | If two-compartment mixing check to be confirmed. Confirm whether Hemosol is used with Prismocitrate or ACD-A |

"Weight indicator effluent": it has been chosen not to install or use reading means at the corresponding receiving station.

Example 4

SCUF: Hydraulic Diagram FIG. 11

| Check | Weight indicator PBP: detector | Weight indicator Dialysate: (pre) detector | Weight indicator Substitution: (pre or post) detector |
|---|---|---|---|
| Presence of solution | Prismocitrate | | |
| Presence of solution | ACD-A | | |
| Presence of solution | Hemosol | | |
| Presence or absence | No recommendation | Mandatory absence | Mandatory absence |
| Function of solution | Drug Possible medical device under physician's responsibility | | |
| Prohibition of nature | No recommendation (or prism0cal not recommended) | | |
| Condition of use | | | |

"Weight indicator effluent": it has been chosen not to install or use reading means at the corresponding receiving station.

Example 5

TPE: Hydraulic Diagram FIG. 12

| Check | Weight indicator PBP: detector | Weight indicator Dialysate: (pre) detector | Weight indicator Substitution: (pre or post) detector |
|---|---|---|---|
| Presence of solution | Prismocitrate | | Plasma |
| Presence of solution | ACD-A | | Plasma |
| Presence of solution | Hemosol | | Plasma |
| Function of solution | Drug, possible medical device under physician's responsibility | | Drug |

-continued

| Check | Weight indicator PBP: detector | Weight indicator Dialysate: (pre) detector | Weight indicator Substitution: (pre or post) detector |
|---|---|---|---|
| Prohibition of nature | No recommendation (or prism0cal not recommended) | | Prohibition of Hemosol, ACD-A, Prismocitrate, Prism0cal |
| Condition of use | | | |

"Weight indicator effluent": it has been chosen not to install or use reading means at the corresponding receiving station.

Example 6

Hemoperfusion: Hydraulic Diagram FIG. 13

| Check | Weight indicator PBP: detector | Weight indicator Dialysate: (pre) detector | Weight indicator Substitution: (pre or post) detector |
|---|---|---|---|
| Presence of solution | Prismocitrate | | |
| Presence of solution | | | |
| Presence of solution | | | |
| Presence of absence | No recommendation | Mandatory absence | Mandatory absence |
| Function of solution | Drug, possible medical device under physician's responsibility | | |
| Prohibition of nature | Prohibition of Prism0cal, Hemosol | | |
| Condition of use | | | |

"Weight indicator effluent": it has been chosen not to install or use reading means at the corresponding receiving station.

Figure 7:
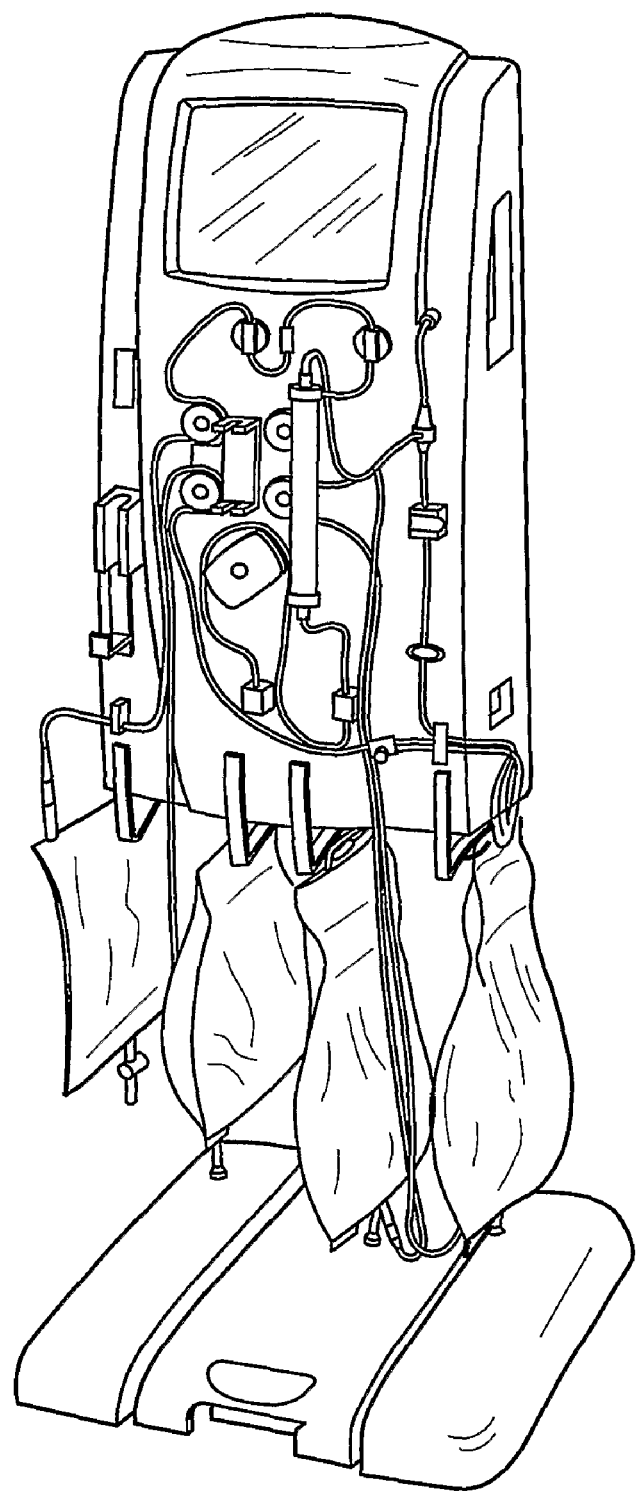
FIG. 7 shows the device according to the invention with the disposable articles (filter, bags and hydraulic connections) installed therein.
Figure 8:
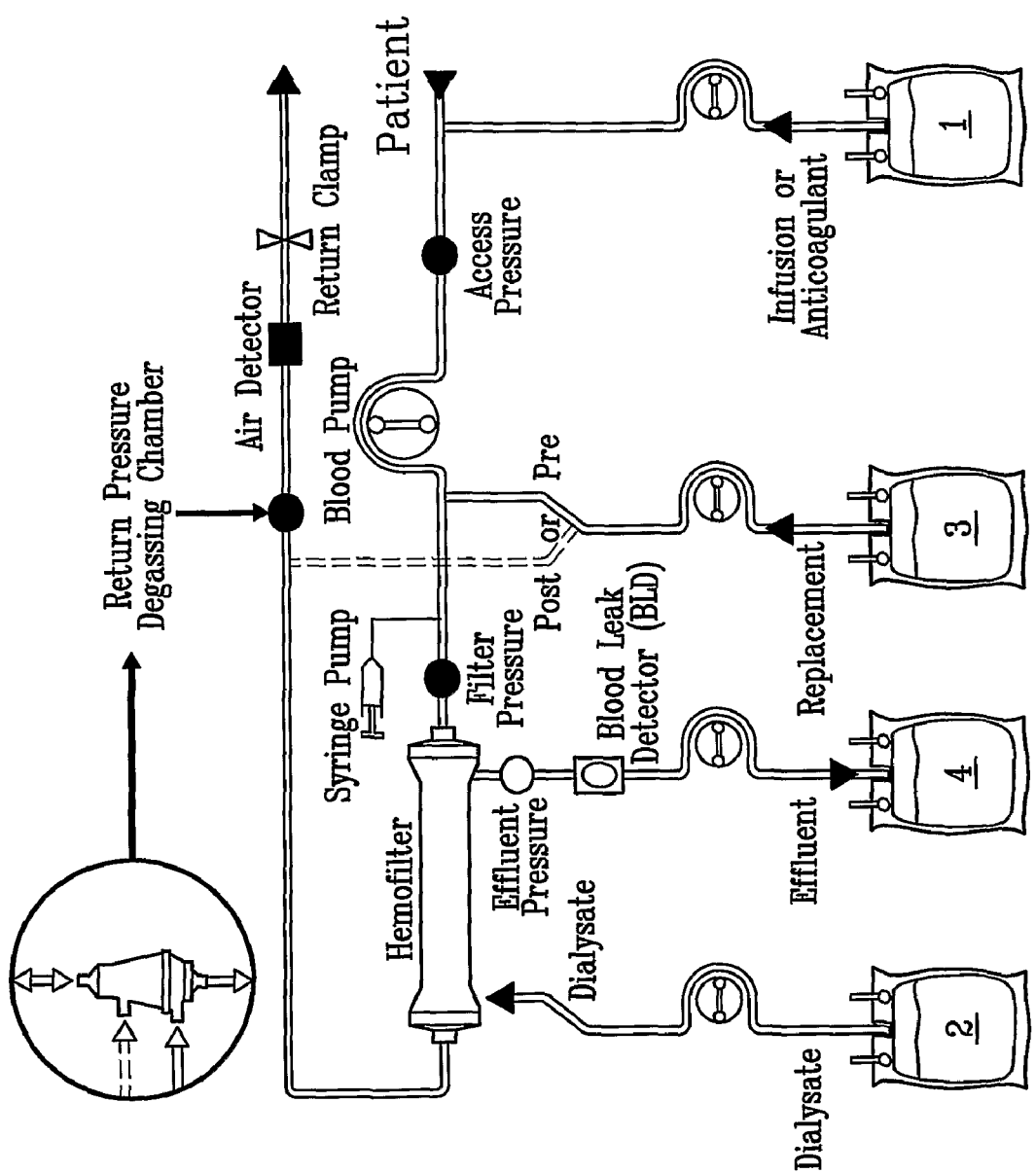
Figure 9:
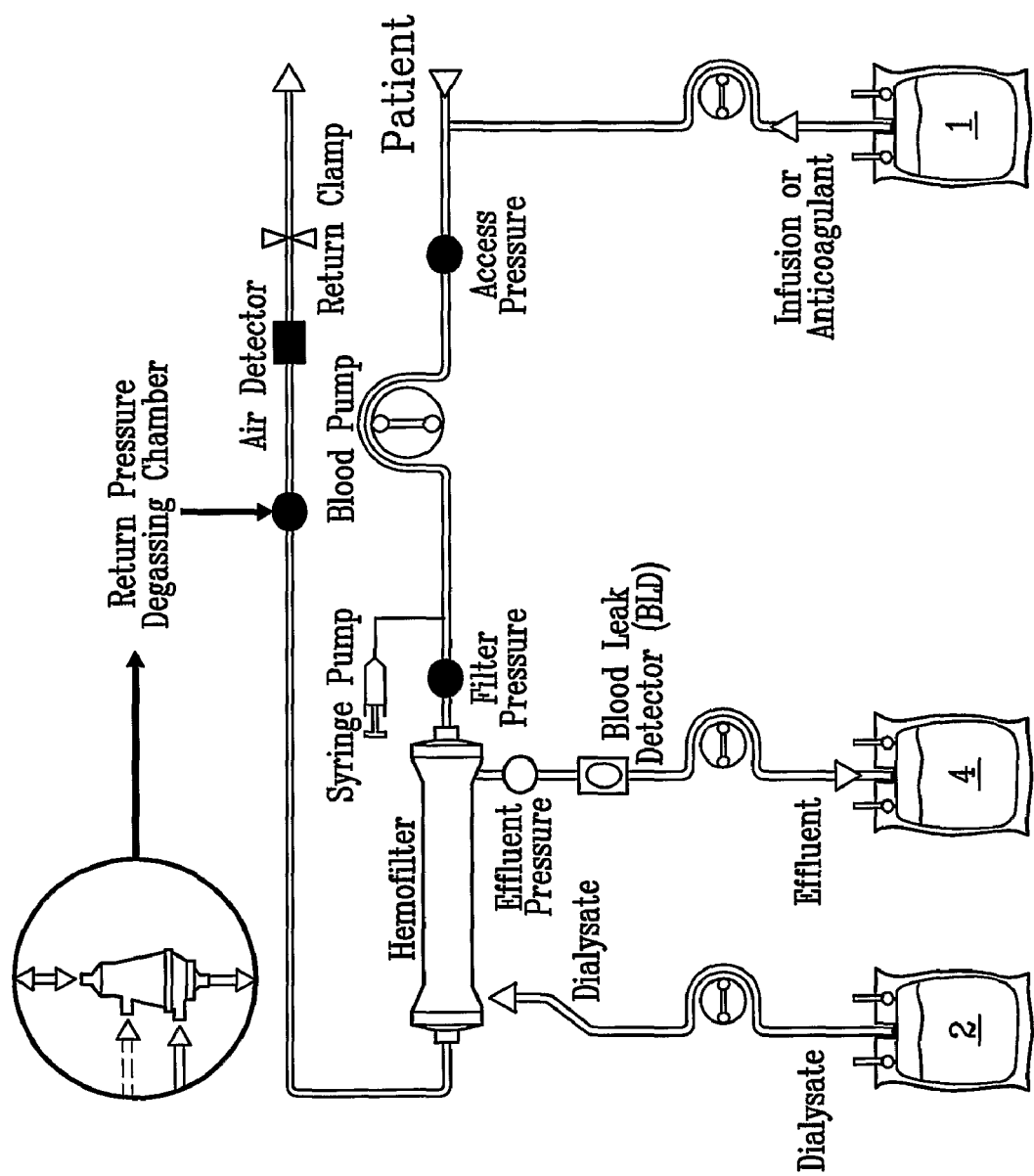
Figure 10:
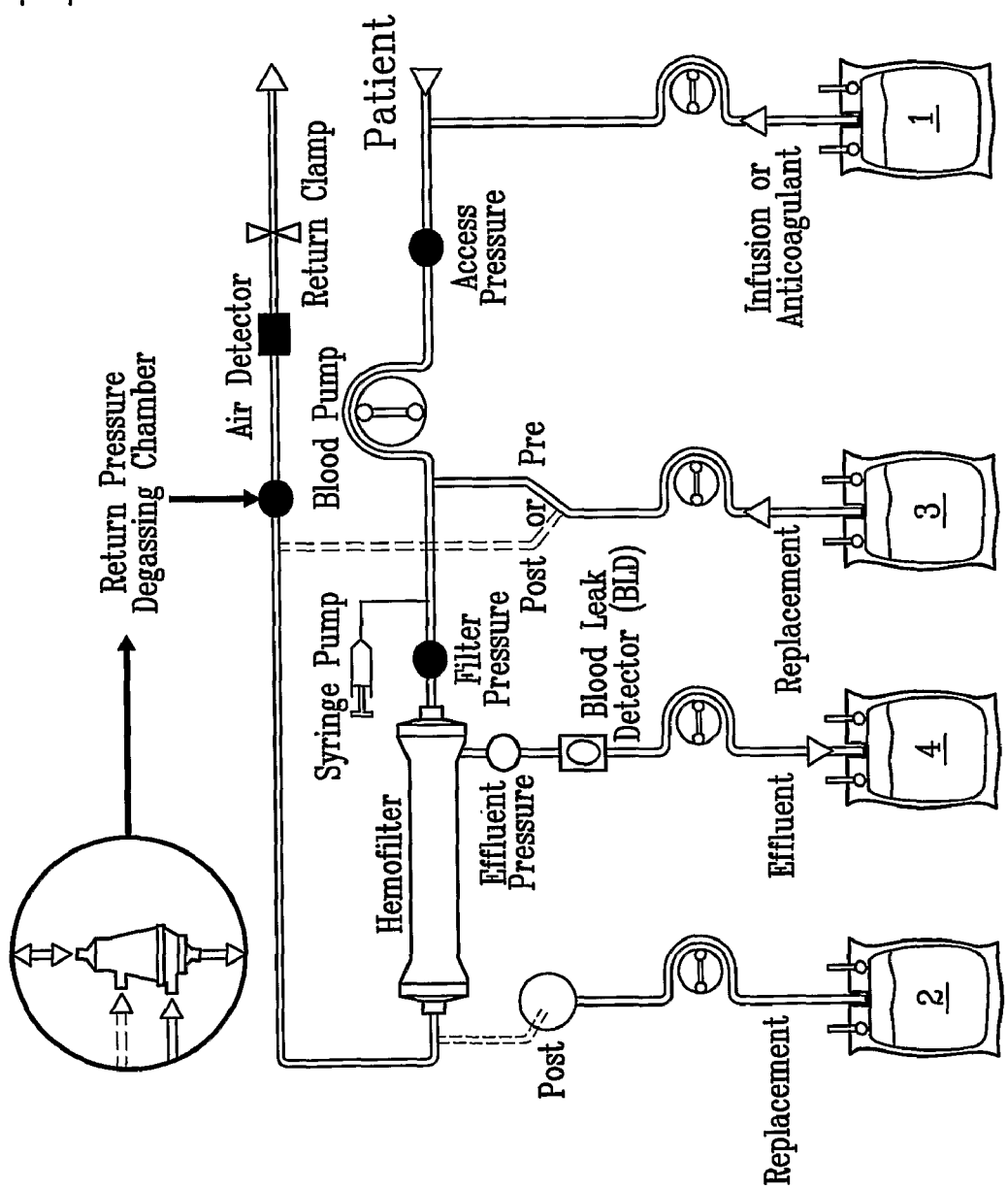
Figure 11:
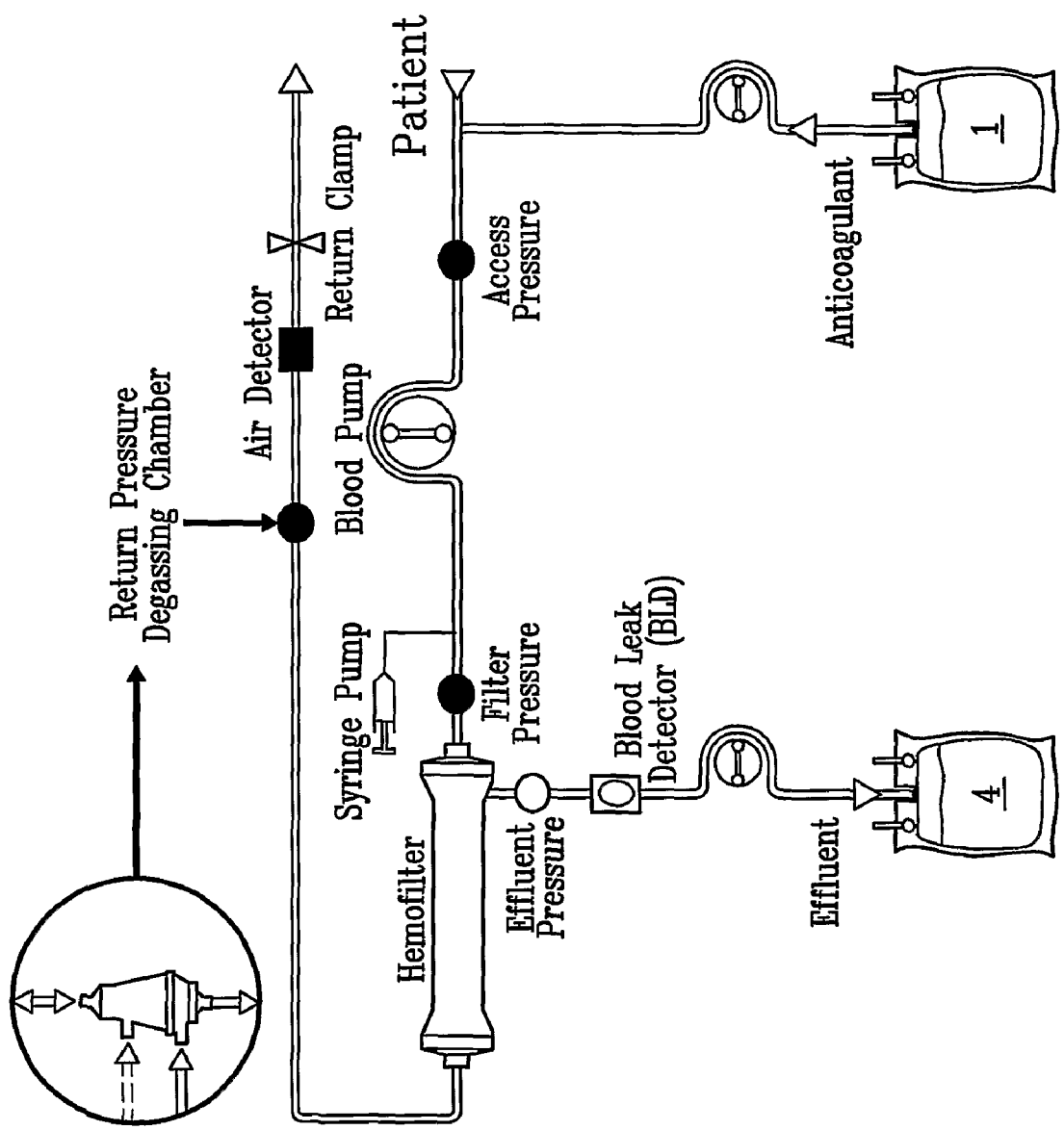
Figure 12:
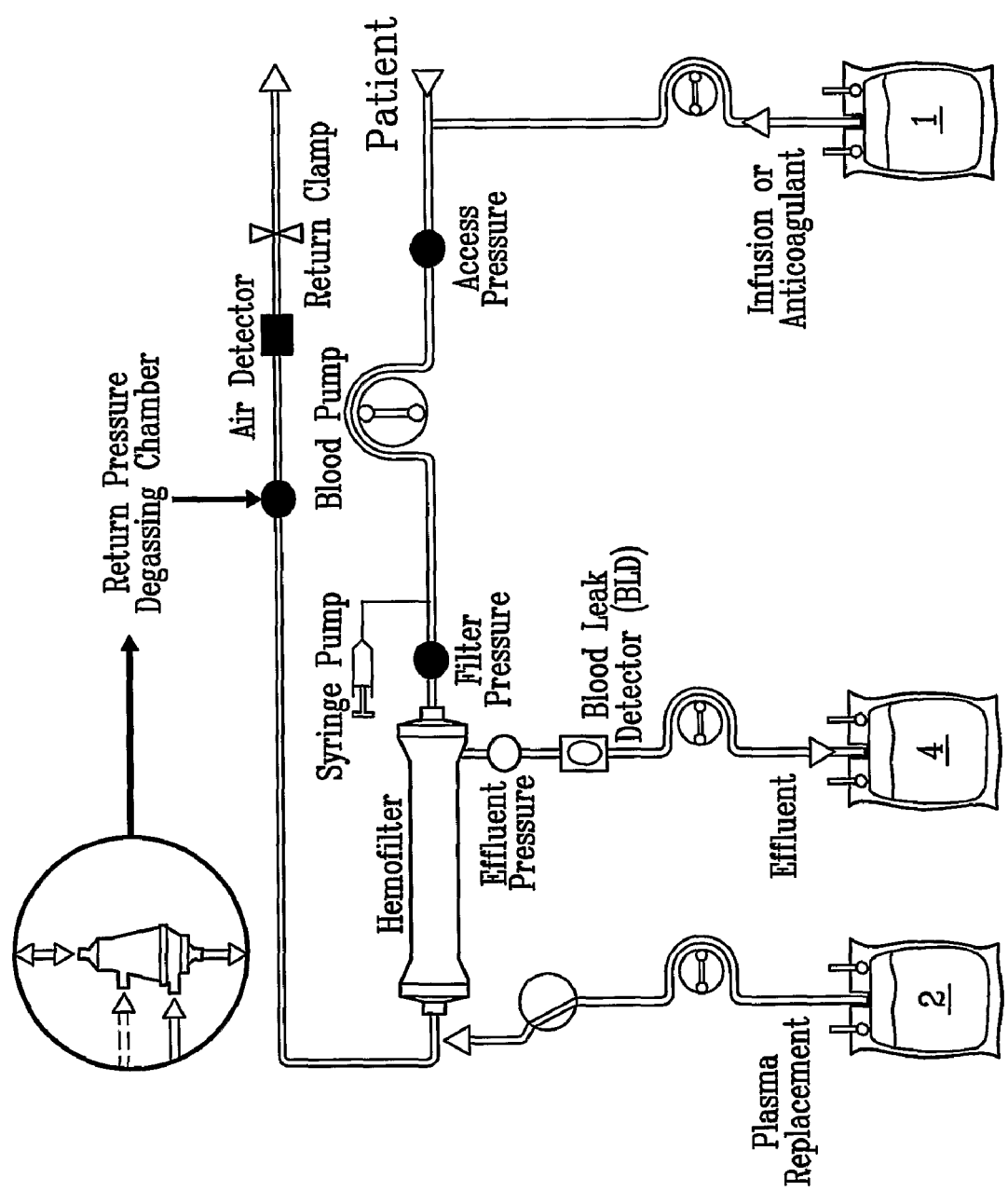

The medical device according to the invention, when using articles, comprises at least one disposable medical article (100) installed in at least one receiving station (2). FIG. 7 shows the device during use, in which four disposable articles (bags) are installed and in which a set is installed, and whose lines are connected to the various bags. These connections and the hydraulic circuits are schematically represented in FIGS. 8 to 13.

The medical device according to the invention has a storage means (101) for disposable articles, which is selected among the following elements: a read-only memory (ROM, EEPROM, . . . ) containing information on the article, a programmable or non-programmable random access memory.

The storage means can be a chip, a color code or bar code tag . . . .

Beyond information on the article, the memory can further be able to receive and store information on the development of the process of use of the device.

The storage means (101) for disposable articles can be fastened in a fixed manner to or into the disposable article (100). They can be for instance sealed, glued, contained in a specific pocket or in the case of a liquid bag, contained in the liquid bag.

The storage means (e.g. RFID Tag) containing the identifier is integral with the bag and the detector associated to the receiving station has a working range inside which it is able to recognize a bag from its identifier.

In case of a two-compartment container, the invention also relates to a container comprising a first compartment containing a first fluid for medical use, at least a second compartment containing a second fluid for medical use, a fluid communication means between the first and second compartment, a closing means for the fluid communication means between the compartments, the closing means being removable so as to enable the communication between the two compartments, characterized in that at least one of the two compartments contains a storage means for storing:
  c. information concerning at least one treatment protocol designed to be executed by the device,
  d. information concerning a configuration of the disposable containers necessary for each treatment protocol at each receiving station,
and in that the storage means is able, once the closing means has been removed from said fluid communication means, to switch from the first to the second compartment.

In this case, if the bag is fastened to the receiving station, the identifier will flow down thanks to its weight towards the second compartment at the bottom of the bag and will be able to be read if the reading means of the station is in low position, and the information about the mixing of the 2 compartments will be inferred. A second identifier can be provided for at the same receiving station, though on the side of the first compartment, which is able to read the storage means in the compartment and to infer the information according to which the two compartments are not in communication with each other.

Moreover, the container can comprise an auxiliary storage means fastened to the container, for storing:
  e. information concerning at least one treatment protocol designed to be executed by the device,
  f. information concerning a configuration of the disposable containers necessary for each treatment protocol at each receiving station.

In this case the receiving station contains a reading means. If the two fluids of the compartments are not mixed, the storage means and the auxiliary storage means are both identified. If the two fluids of the compartments are mixed, then only one identifier is detected and the absence of the other identifier indicates that it is at the bottom of the bag.

In this case the fluid communication means can be a tube connecting each compartment to the other, and the closing means can be a piece crossing the tube section. As an alternative, the closing means can be a seal between the two compartments (in case of one bag, a seal defines two compartments), which by pulling one of the two compartments gives out and unseals so as to create a communication between the two compartments.

For a two-compartment container of the type two-compartment bag, having a small pocket close to the fastening means and a large pocket under the small pocket, a RFID Tag can be placed inside the small pocket so that when detected the machine can infer that the 2 compartments are not mixed since it is still inside the pocket close to the reading means. When the 2 compartments are mixed, the RFID Tag "sinks" to the bottom of the bag and its absence indicates that the 2 compartments have been mixed.

The storage means (101) can comprise at least one of the following data concerning the disposable article associated thereto:
the nature of the article,
the effectiveness parameters of the article (for a dialyzer the fluid exchange surface . . . ),
the function of the article,
the medical classification of the article (drug, medical device, class . . . ),
the date of expiry of the article,
the groups of patients who do not tolerate the use of the article or the administration of its content,
the manufacturer of the article,
the manufacturing date of the article,
the modes of use of the article (e.g. the other medical articles that must not be combined with the article taken into consideration, or the maximum duration of use of the article from its installation),
the volume contained in the compartment or compartments,
and any other parameter useful to get information about the article, its use and limitations.

The invention relates a kit of containers (100, 100', 100", 100''') for liquids for medical use, this kit being designed to be used and fastened onto a medical device (1) so as to provide a plurality of extracorporeal blood or plasma treatments, comprising several receiving stations (2, 2' . . . ) for containers having each a fastening means (5, 5', . . . ) for containers, the fastening means for containers being identical, each station having a reading means (3, 3', . . . ) associated thereto so as to identify the container to be received, and wherein:

Each container is provided with a storage means (101, 101' . . . ) for storing:
c. information concerning at least one treatment protocol designed to be executed by the device,
d. information concerning a configuration of the disposable containers necessary for each treatment protocol at each receiving station.

The kit of containers according to the invention can comprise the following containers:
a container filled with dialysis liquid,
a container filled with perfusion liquid,
a container filled with anticoagulant,
an empty container for receiving used liquid.

What has been described herein about medical articles applies to the kit according to the invention.

The invention also relates to a control method for the device (1) according to the invention, wherein at least one disposable medical article (100) is installed in at least one of the receiving stations (2), the device comprising an interface (12), the method comprising at least the following steps:
receiving by way of the interface (12) the selection of an extracorporeal treatment among the plurality of possible treatments stored,
reading the storage means (101) for each disposable article installed in the receiving station or stations (5) by way of each reading means (3) associated thereto,
comparing the installation configuration of the articles once they are installed in the receiving stations with the required stored configuration of disposable articles necessary for the selected treatment,
sending by way of the display means (13) an alarm or warning signal when the configuration of the installed articles does not correspond to the required stored configuration.

The control method according to the invention can include the sending of the signal comprising one of the following warnings:
a warning if a necessary article is missing in the device,
a warning if an unnecessary article is present in the device,
a warning if a necessary article is present but is installed in an incorrect receiving station,
a warning if a necessary article is present in the device,
a warning if a present article requires a particular use, e.g. a preparation previous to the use of the article.

The invention further relates to a method for installing disposable articles in a device according to the invention, comprising the following steps:
selecting an extracorporeal treatment among the plurality of possible stored treatments,
installing the medical article or articles (100 . . . ) in the receiving station or stations (2 . . . ),
reading the storage means (101 . . . ) for each disposable article installed in the receiving station or stations (2 . . . ) by way of each reading means (3 . . . ) associated thereto,
comparing the configuration of the articles installed in the receiving stations with the required stored configuration of disposable articles for the selected treatment,
if the configuration of the installed articles is not identical to the required stored configuration, sending an alarm or warning signal,
as a function of the sending of an alarm or warning message, add, remove or change at least one disposable medical article.

The invention claimed is:
1. A medical device for providing a plurality of extracorporeal blood or plasma treatments in a filtration unit having a primary compartment and a secondary compartment, which are separated by a semipermeable membrane, the primary compartment being able to be connected to a primary extracorporeal blood circuit, the secondary compartment being able to be connected to a secondary circuit, the primary circuit and the secondary circuit defining an extracorporeal circuit, the device being apt to receive at least one disposable article that can be connected to the extracorporeal circuit, each disposable article being equipped with storage means containing information about the disposable article, the device comprising:
a first receiving station for disposable articles, which is able to collect a first disposable article,
a first reading means associated to the first station for identifying a disposable article received at the first station,
at least a second station for receiving disposable articles, which is able to collect a second similar disposable article,
at least a second reading means associated to the second station for identifying a disposable article received at the second station,
a device storage means for storing:
information concerning at least one treatment protocol designed to be executed by the device,
information concerning a configuration of the disposable articles necessary for each treatment protocol at each receiving station,
a control unit connected to the device storage means, comprising:

means for receiving information concerning the treatment protocols to be executed, means for receiving information read by at least one of the reading means, and means for checking, as a function of this information, whether the configuration of the disposable article or articles received complies with the stored configuration for the treatment to be executed.

2. The device according to claim 1, wherein the configuration of the disposable articles necessary for each protocol comprises at least one of the following elements for each protocol: the number of necessary articles, the nature of each necessary article, the function of each necessary article, the position of each necessary article at each receiving station.

3. The device according to claim 1, wherein the first receiving station comprising first fastening means for articles, wherein at least the second receiving station for articles comprises second fastening means for articles that are identical to the first fastening means for articles.

4. The device according to claim 1, wherein the disposable article received at the first receiving station comprises first fastening means to a receiving station, at least the second disposable article received at the second receiving station comprises second fastening means to a receiving station that are identical to the first fastening means of the station.

5. The device according to claim 1, wherein the control unit (10) comprises means for sending, as a function of said information, an alarm signal when the configuration of the disposable article or articles received does not comply with the configuration of the selected treatment.

6. The device according to claim 1, comprising display means, and wherein the control unit comprises means for controlling, as a function of said information, said display means for displaying an alarm or warning signal comprising at least one of the following information:
   a necessary article is missing in the device,
   an unnecessary article is present in the device,
   a necessary article is present but is installed in an incorrect receiving station,
   a necessary article is present in the device,
   a present article requires a particular use, optionally wherein the particular use is a preparation previous to the use of the article.

7. The device according to claim 1, wherein the device storage means are able to store all the information received by the reading means associated to the receiving stations.

8. The device according to claim 1, wherein at least one reading means is integrated into the associated receiving station.

9. The device according to claim 1, wherein at least one reading means is close to the associated receiving station.

10. The device according to claim 1, wherein at least one receiving station is a weighing means for weighing the disposable article to be received.

11. The device according to claim 1, wherein at least one reading means is a contactless reading means.

12. The device according to claim 11, wherein the contactless reading means is at least one of the following readers: a radiofrequency reading means, an optical reader, a magnetic reader.

13. The device according to claim 1, wherein the disposable articles belong to one of the following categories:
   container comprising a medical liquid,
   empty container designed to receive used liquid,
   dialyzer,
   set containing at least one filter with various accesses and lines connected to the accesses of the filter so as to form at least partially the extracorporeal circuit,
   blood or plasma filter, absorption cartridge,
   ultrafilter,
   plasma filter.

14. The device according to claim 13, wherein the category of containers comprising a medical liquid is a bag, and wherein the disposable articles comprise at least one of the following bags: a bag filled with dialysis liquid, a bag filled with perfusion liquid, a bag filled with anticoagulant, an empty bag for receiving used medical liquid during treatment.

15. The device according to claim 13, wherein at least one of the disposable articles is a container provided with at least two compartments, the compartments containing each a liquid for medical use, and wherein a mode of previous use of this container is the mixing of the liquids immediately before its use in the device.

16. The device according to claim 1, comprising:
   a plurality of first receiving stations comprising first respective identical fastening means for fastening a first category of disposable articles,
   at least a plurality of second receiving stations comprising second respective identical fastening means for fastening a second category of disposable articles, the second fastening means being different from the first fastening means,
   wherein the first category and the second category of disposable articles are each included among one of the following categories:
   container comprising a medical liquid,
   empty container designed to receive used liquid,
   dialyzer,
   set comprising at least one filter containing various accesses and lines connected to the accesses of the filter so as to form at least partially the extracorporeal circuit,
   blood or plasma filter, absorption cartridge,
   ultrafilter,
   plasma filter.

17. The device according to claim 1, wherein:
   the first receiving station is designed to receive a container for perfusion liquid to be connected to the arterial line of the primary circuit,
   the second receiving station is designed to receive a container for fresh dialysis liquid to be connected to the inlet of the secondary compartment of the filtration unit,
   the device also comprising:
   a third receiving station for disposable articles, similar to the first and second receiving stations and designed to receive a third disposable article, the third article being a container for perfusion liquid to be connected to the primary circuit upstream or downstream from the first compartment of the filtration unit,
   at least one third reading means associated to the third station for identifying the disposable article received at the third station,
   a fourth receiving station for disposable articles, similar to the first three receiving stations and designed to collect an empty fluid container to be connected to the outlet of the secondary compartment of the filtration unit.

18. The device according to claim 17, wherein the storage means comprise at least one of the following protocols:
   first protocol of treatment by hemodiafiltration requiring the presence of four medical articles on the four corresponding receiving stations, second protocol of treatment by hemodialysis requiring the presence of the first, second and fourth medical article on the corresponding first, second and third receiving station, third protocol of treatment by hemofiltration requiring the presence of the four medical articles on the four corresponding receiving stations, fourth protocol of treatment by ultrafiltration requiring the presence of the first and fourth medical article on the corresponding first and fourth receiving station, fifth treatment protocol by plasma exchange requiring the presence of the first, second and fourth medical article on the corresponding first, second and fourth receiving station, sixth protocol of treatment by hemoperfusion requiring the presence of the first medical article on the corresponding fourth receiving station.

19. The medical device according to claim 1, wherein at least one disposable medical article is installed in at least one receiving station.

20. The device according to claim 19, wherein the storage means for disposable articles is included among the following elements: a read-only memory containing information on the article, a programmable or non-programmable random access memory, a random access memory where data concerning the development of the treatment can be written.

21. The medical device according to claim 19, wherein the storage means for disposable articles are fastened in a fixed manner to or into the disposable article.

22. The medical device according to claim 19, wherein the storage means comprise at least one of the following data concerning the disposable article associated thereto:
a nature of the article,
an effectiveness parameters of the article,
a function of the article,
a medical classification of the article,
a date of expiry of the article,
groups of patients who do not tolerate a use of the article or an administration of its content,
a manufacturer of the article,
a manufacturing date of the article,
modes of use of the article,
a volume contained in the articles of container type.

23. A kit of containers for liquids for medical use, this kit being designed to be used and fastened in a medical device so as to provide a plurality of extracorporeal blood or plasma treatments, and which comprises several receiving stations for containers having each a fastening means for containers, the fastening means for containers being identical, each station having an associated reading means for identifying the container to be received, and wherein:
Each container is equipped with a storage means for storing:
a. information concerning at least one treatment protocol designed to be executed by the device,
b. information concerning a configuration of the disposable containers necessary for each treatment protocol at each receiving station.

24. The kit of containers according to claim 23, comprising the following containers:
a container filled with dialysis liquid,
a container filled with perfusion liquid,
a container filled with anticoagulant,
an empty container for receiving used liquid.

25. A container comprising a first compartment containing a first fluid for medical use, at least a second compartment containing a second fluid for medical use, a fluid communication means between the first and second compartment, a closing means for the fluid communication means between the compartments, the closing means being removable so as to enable the communication between the two compartments, characterized in that at least one of the two compartments contains a storage means for storing:
a. information concerning at least one treatment protocol designed to be executed by the device,
b. information concerning a configuration of the disposable containers necessary for each treatment protocol at each receiving station, and in that the storage means is able, once the closing means has been removed from said fluid communication means, to switch from the first to the second compartment.

26. The container according to claim 25, comprising an auxiliary storage means fastened to the container, for storing:
a. information concerning at least one treatment protocol designed to be executed by the device,
b. information concerning a configuration of the disposable containers necessary for each treatment protocol at each receiving station.

27. A control method for the device according to claim 1, wherein at least one disposable medical article is installed in at least one of the receiving stations, the device comprising an interface, the method comprising at least the following steps:
receiving by way of the interface the selection of an extracorporeal treatment among the plurality of possible treatments stored,
reading the storage means for each disposable article installed in the receiving station or stations by way of each reading means associated thereto,
comparing an installation configuration of the articles once they are installed in the receiving stations with the required stored configuration of disposable articles necessary for the selected treatment,
sending by way of the display means an alarm or warning signal when the configuration of the installed articles does not correspond to the required stored configuration.

28. The control method according to claim 27, wherein the sending of the signal comprises one of the following warnings:
a warning if a necessary article is missing in the device,
a warning if an unnecessary article is present in the device,
a warning if a necessary article is present but is installed in an incorrect receiving station,
a warning if a necessary article is present in the device,
a warning if a present article requires a particular use, optionally wherein the particular use is a preparation previous to the use of the article.

29. A method for installing disposable articles in a device according to claim 1, comprising the following steps:
selecting an extracorporeal treatment among the plurality of possible stored treatments,
installing the medical article or articles in the receiving station or stations,
reading the storage means for each disposable article installed in the receiving station or stations by way of each reading means associated thereto,
comparing the configuration of the articles installed in the receiving stations with the required stored configuration of disposable articles for the selected treatment,
if the configuration of the installed articles is not identical to the required stored configuration, sending an alarm or warning signal,
as a function of the sending of an alarm or warning message, add, remove or change at least one disposable medical article.

30. A medical device for providing a plurality of extracorporeal blood or plasma treatments in a filtration unit having a primary compartment and a secondary compartment, which are separated by a semipermeable membrane, the primary compartment being able to be connected to a primary extracorporeal blood circuit, the secondary compartment being able to be connected to a secondary circuit, the primary circuit and the secondary circuit defining an extracorporeal circuit, the device being apt to receive at least one disposable article that can be connected to the extracorporeal circuit, each disposable article being equipped with storage means containing information about the disposable article, the device comprising:

- a first receiving station for disposable articles, which is designed to receive a container for perfusion liquid to be connected to an arterial line of the primary circuit,
- a first reading means associated to the first station for identifying a disposable article received at the first station,
- at least a second station for receiving disposable articles, which is designed to receive a container for fresh dialysis liquid to be connected to an inlet of the secondary compartment of the filtration unit,
- at least a second reading means associated to the second station for identifying a disposable article received at the second station,
- a third receiving station for disposable articles, similar to the first and second receiving stations and designed to receive a third disposable article, the third article being a container for perfusion liquid to be connected to the primary circuit upstream or downstream from the primary compartment of the filtration unit,
- at least one third reading means associated to the third station for identifying the disposable article received at the third station,
- a fourth receiving station for disposable articles, similar to the first, second, and third receiving stations and designed to collect an empty fluid container to be connected to an outlet of the secondary compartment of the filtration unit;
- a device storage means for storing:
  - information concerning at least one of the following treatment protocols designed to be executed by the device:
    - first protocol of treatment by hemodiafiltration requiring the presence of four medical articles on the four corresponding receiving stations,
    - second protocol of treatment by hemodialysis requiring the presence of the first, second and fourth medical article on the corresponding first, second and third receiving station,
    - third protocol of treatment by hemofiltration requiring the presence of the four medical articles on the four corresponding receiving stations,
    - fourth protocol of treatment by ultrafiltration requiring the presence of the first and fourth medical article on the corresponding first and fourth receiving station,
    - fifth treatment protocol by plasma exchange requiring the presence of the first, second and fourth medical article on the corresponding first, second and fourth receiving station,
    - sixth protocol of treatment by hemoperfusion requiring the presence of the first medical article on the corresponding fourth receiving station,
  - information concerning a configuration of the disposable articles necessary for each treatment protocol at each receiving station,
- a control unit connected to the device storage means, comprising:
  - means for receiving information concerning the treatment protocols to be executed,
  - means for receiving information read by at least one of the reading means, and
  - means for checking, as a function of this information, whether the configuration of the disposable article or articles received complies with the stored configuration for the treatment to be executed.

* * * * *

UNITED STATES PATENT AND TRADEMARK OFFICE
CERTIFICATE OF CORRECTION

PATENT NO. : 8,400,298 B2  Page 1 of 1
APPLICATION NO. : 12/809032
DATED : March 19, 2013
INVENTOR(S) : Hiram Rada It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 373 days.

Signed and Sealed this
First Day of September, 2015

Michelle K. Lee
*Director of the United States Patent and Trademark Office*